United States Patent
Wei et al.

(10) Patent No.: US 6,688,744 B2
(45) Date of Patent: *Feb. 10, 2004

(54) BACK PROJECTION VISUAL FIELD TESTER

(75) Inventors: Jay Wei, Fremont, CA (US); Jianping Wei, Pleasanton, CA (US); Christopher J. R. V. Baker, Moraga, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/016,536

(22) Filed: Dec. 10, 2001

(65) Prior Publication Data

US 2003/0007121 A1 Jan. 9, 2003

Related U.S. Application Data

(63) Continuation-in-part of application No. 09/884,507, filed on Jun. 14, 2001, now Pat. No. 6,572,229.

(51) Int. Cl.[7] .................................................. A61B 3/14
(52) U.S. Cl. ...................................................... 351/206
(58) Field of Search ................................. 351/200, 205, 351/211, 221, 222, 224, 226, 237, 239, 240, 241, 242, 243; 359/443, 445, 456, 451, 457, 460

(56) References Cited

U.S. PATENT DOCUMENTS

| | | | |
|---|---|---|---|
| 4,361,382 A | 11/1982 | Miyoshi et al. | 350/126 |
| 4,626,090 A | 12/1986 | Charlier et al. | 351/226 |
| 5,024,519 A | 6/1991 | Howard et al. | 351/226 |
| 5,046,835 A | 9/1991 | Billeter et al. | 351/206 |
| 5,323,194 A | 6/1994 | Campbell et al. | 351/226 |
| 5,459,536 A | 10/1995 | Shalon et al. | 351/226 |
| 5,717,481 A | 2/1998 | Obata et al. | 351/224 |
| 5,870,169 A | 2/1999 | Koest | 351/225 |
| 6,139,150 A | 10/2000 | Wei | 351/11 |
| 6,315,412 B1 | 11/2001 | Snodderly et al. | 351/200 |
| 6,347,012 B1 | 2/2002 | Monson et al. | 359/451 |
| 6,414,727 B1 | 7/2002 | Benton | 348/744 |
| 6,454,412 B1 * | 9/2002 | Torrey | 351/243 |

\* cited by examiner

*Primary Examiner*—George Manuel
(74) *Attorney, Agent, or Firm*—Michael B. Einschlag

(57) ABSTRACT

One embodiment of the present invention is a visual field tester that includes: (a) a projection screen; (b) a stimulus projection system that projects a light stimulus onto a first side of the projection screen; (c) a background projection system that projects a background light onto the first side of the projection screen; and (d) a lens system disposed on a second side of the projection screen that directs light transmitted through the projection screen to a predetermined location.

27 Claims, 5 Drawing Sheets

Numerical aperture

BACK PROJECTION VISUAL FIELD TESTER

This is a continuation-in-part of a patent application entitled "Back Projection Visual Field Tester" having Ser. No. 09/884,507 now U.S. Pat. No. 6,572,229 which was filed on Jun. 14, 2001.

TECHNICAL FIELD OF THE INVENTION

The present invention pertains to an optical apparatus for visual field testing. In particular, the present invention relates to an optical apparatus for visual field testing using a back projection system.

BACKGROUND OF THE INVENTION

A visual field tester is an apparatus that is used to test, among other things, the peripheral vision of a human eye—such an apparatus has been known in the art for many years. Test results from visual field testers are used to diagnosis diseases that cause degradation of vision sensitivity. For example, a Standard Automated Perimeter (SAP), one of the most accepted of such testing apparatus, typically performs brightness contrast sensitivity tests over a large visual field.

In prior art visual field testers used to perform a contrast sensitivity test, it is common to include a hemispherical projection surface and a stimulus optical projection system. In a typical such visual field tester, the hemispherical projection surface is uniformly illuminated (for example, using a white light source) to provide a constant and uniform background illumination—the aim is that the hemispherical projection surface be a Lambertian illumination surface (i.e., a surface upon which brightness is constant over different viewing angles). In a typical such visual field tester, the stimulus optical projection system presents stimuli (typically in the form of a circular spot) at selected points on an internal surface of the hemispherical projection surface. For example, this is done by sequentially flashing images of light sources on the internal surface of the hemispherical projection surface where the position and brightness of the stimuli are specified by a computer implemented algorithm. In use for testing, a patient's eye is placed at, or close, to a center of a surface of a volume enclosed by the hemispherical projection surface, and the patient is asked to respond to the stimuli by pressing, for example, a mouse button. Then, the contrast sensitivity of the patient's visual field is mapped by changing the brightness and position of the stimuli on the constant, uniform background illumination, and recording the patient's response thereto. However, such prior art devices have a drawback in that they are bulky and expensive. In particular, the radius of the hemispherical projection surface is typically set to about 30 cm to enable the patient to see the stimulus comfortably (i.e., without straining the patient's test eye).

U.S. Pat. No. 5,870,169 (the '169 patent) discloses a visual field tester that utilizes a hemispherical surface in an alternative manner to that described above. Specifically, instead of projecting a stimulus onto an internal surface of a hemispherical projection surface from the patient's side, as disclosed in the '169 patent, a rear projection device is used to project a stimulus onto an external surface of a hemispherical projection surface. In this case, the hemispherical projection surface is comprised of a transparent material, and the patient can see the stimulus when it is viewed from the interior surface of the hemispherical projection surface. The apparatus in the '169 patent provides a stimulus having an improved shape and brightness uniformity over the apparatus's 72-degree visual field when compared with the shape and brightness uniformity of prior visual field testers. Since there are moving mechanisms on the back of the projection surface, the background illumination is provided from the front side of the projection surface. Therefore, the projection surface has to be coated with an absorbing material to reflect the background illumination from the front side. However, due to absorption by the absorbing material, the maximum brightness of the stimulus is reduced.

Another visual field tester is disclosed in U.S. Pat. No. 5,046,835 (the '835 patent). As disclosed in the '835 patent, the size of a visual field tester can be reduced by using a cupola-less optical system. In particular, the '835 patent discloses a direct viewing optical system that projects a stimulus directly into a patient's eye. To do this, the optical system images a light source onto an intermediate image plane of an eyepiece (to serve as a stimulus), and separately images light output from a diffused light source onto the intermediate image plane (to serve as a uniformly illuminated background). Then, the stimulus and the background are combined through a beamsplitter, and projected onto the patient's retina. In use, the patient views a test field through large field of view (60 degrees), long working-distance eyepieces. Because the apparatus disclosed in the '835 patent does not utilize a hemispherical projection surface, the size of the apparatus is significantly reduced. However, the cost of a large field of view, long working-distance eyepiece is increased due the aperture size of the lens.

U.S. Pat. No. 6,139,150 discloses a visual field tester that uses a retro-reflector array to eliminate use of an eyepiece. As a result, the visual field tester has reduced cost and complexity when compared with the above-described apparatus. However, it is difficult to manufacture a retro-reflector array having a quality that is as high as is required to perform a visual field test.

In light of the above, there is a need in the art for further visual field testers that can, for example, provide an SAP test in a cost-effective way.

SUMMARY OF THE INVENTION

One or more embodiments of the present invention advantageously satisfy the above-identified need in the art, and provide a back projection visual field tester. Specifically, one embodiment of the present invention is a visual field tester of a patient's eye that comprises: (a) a projection screen; (b) a stimulus projection system that projects a light stimulus onto a first side of the projection screen; (c) a background projection system that projects a background light onto the first side of the projection screen; and (d) a lens system disposed on a second side of the projection screen that directs light transmitted through the projection screen to the patient's eye.

DETAILED DESCRIPTION

Figure 1A:
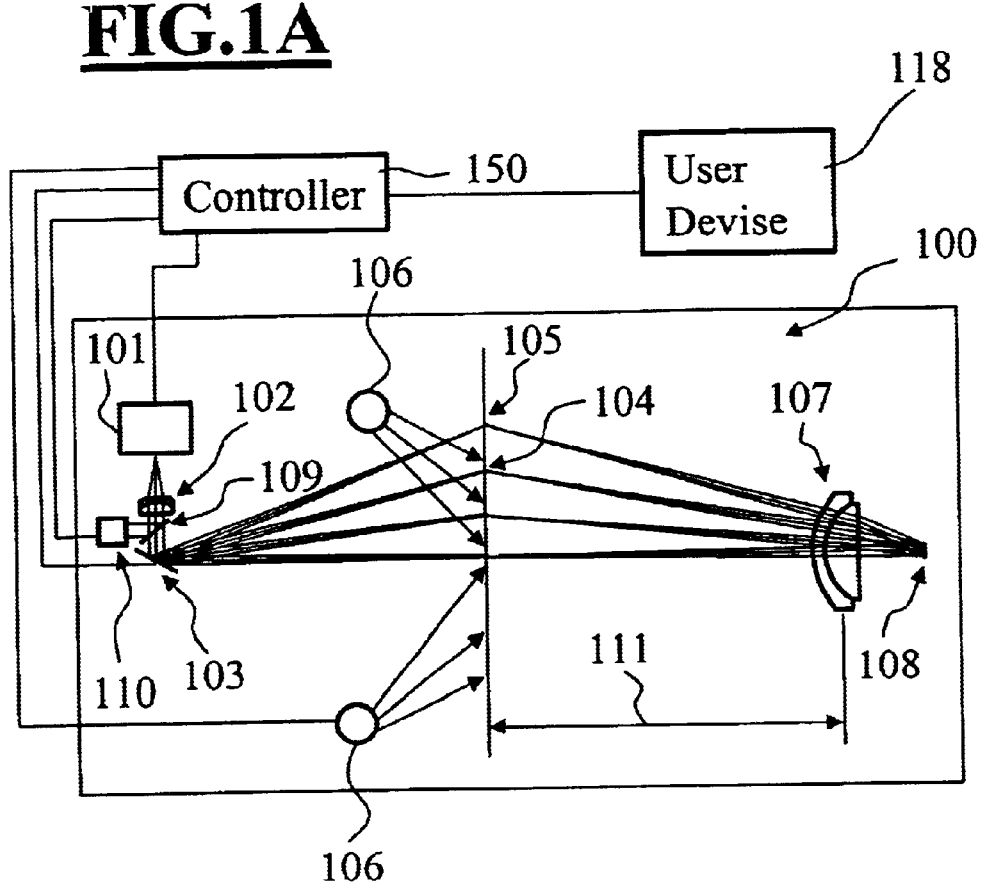
FIG. 1A shows a block diagram of one embodiment of a back projection visual field tester that is fabricated in accordance with the present invention.

FIG. 1A shows a block diagram of back projection visual field tester 100 that is fabricated in accordance with one embodiment of the present invention. As shown in FIG. 1A, a stimulus projection system for back projection visual field tester 100 comprises light source 101 and stimulus projection lens system 102 (those of ordinary skill in the art will readily understand that stimulus projection lens system 102 may comprise one or more lenses). In use, an aperture (not shown) of light source 101 is imaged by stimulus projection lens system 102 onto projection screen 105 (embodiments of projection screen 105 will be described below in conjunction with FIGS. 3A and 3B) to provide a stimulus (in FIG. 1A, the stimulus is shown at various positions as stimuli 104 to illustrate that the stimulus may be presented to a patient at various positions on projection screen 105). Light source 101 may include an LED, a Halogen lamp, a short arc Mercury lamp, a Xenon lamp, a laser, or any other suitable light source. The shape of the stimulus may be circular (a typical visual field tester utilizes a circular spot), or it may be any other shape, which shape can be provided by utilizing an aperture for light source 101 in accordance with any one of a number of methods and apparatus that are well known to those of ordinary skill in the art. Further, the shape of the stimulus may be changed under the control of controller 150 (for example, a computer such as a PC) by changing the aperture and/or its shape in accordance with any one of a number of methods and apparatus that are well known to those of ordinary skill in the art. Still further, an interface apparatus (not shown) is disposed between controller 150 and light source 101 in a manner which is well known to those of ordinary skill in the art. Then, in accordance with methods that are well known to those of ordinary skill in the art, for example, under software control, controller 150 sends signals through the interface apparatus to light source 101 to cause it to emit light. In accordance with methods that are well known to those of ordinary skill in the art, controller 150, under software control, controls output from light source 101 as to one or more of: (a) duration of an illumination interval; (b) intensity of illumination during the illumination interval; and (c) color. For example, color may be controlled by use of filters in a manner that is well known to those of ordinary skill in the art. Further, the control input for controller 150 can result from predetermined criteria and/or from user input by means of a user interface (not shown) in accordance with any one of a number of methods that are well known to those of ordinary skill in the art.

As further shown in FIG. 1A, beamsplitter 109 is disposed in an optical path of the stimulus projection system, and beamsplitter 109 directs a portion of the light output from light source 101 to photodetector 110. Output from photodetector 109 is applied as input to controller 150, and controller 150 utilizes this input to monitor, among other things, the brightness of the stimulus. Many methods and apparatus are well known to those of ordinary skill in the art for fabricating beamsplitter 109 and photodetector 110.

As further shown in FIG. 1A, light passing through beamsplitter 109 impinges upon scanner system 103, and is directed by scanner system 103 to impinge on projection screen 105 at various positions across the surface thereof. An interface apparatus (not shown) is disposed between controller 150 and scanner system 103 in a manner that is well known to those of ordinary skill in the art. Then, in accordance with methods that are well known to those of ordinary skill in the art, for example, under software control, controller 150 sends signals through the interface apparatus to scanner system 103 to cause scanner system 103 to move and, thereby, to scan the light incident thereon over the surface of projection screen 105. As shown in FIG. 1A, scanner system 103 comprises gimbal-mounted, turning mirror 103. Many methods are well known to those of ordinary skill in the art for use in fabricating a controller-controlled scanner, and in particular, a controller-controlled, gimbal-mounted, turning mirror. For example, a suitable gimbal-mounted, turning mirror apparatus is manufactured by the Newport Corporation of Irvine Calif.

Since back projection field tester 100 shown in FIG. 1A utilizes gimbal-mounted, turning mirror 103 to move the stimulus to various positions on projection screen 105 to provide stimuli 104, stimuli 104 will be focused over a spherical surface whose radius is determined by movement of turning mirror 103. As a result, the depth of focus of stimulus projection lens system 102 should be designed to be large enough so that stimuli 104 are substantially in focus over the useful scan rage. Thus, the numerical aperture of stimulus projection lens system 102 should be small enough to provide the desired depth of field.

Figure 1B:
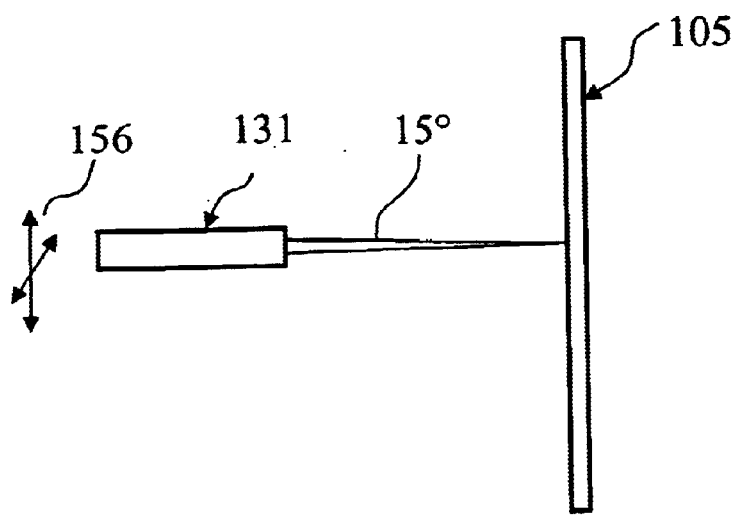
FIG. 1B shows a block diagram of an alternative embodiment of a stimulus projection system that can be utilized to fabricate a back projection visual field tester in accordance with one or more embodiments of the present invention.

Embodiments of the present invention are not limited to the use of a gimbal-mounted, turning mirror. For example, instead of using gimbal-mounted, turning mirror 103 to control the position of the stimulus (see stimuli 104 in FIG. 1A), alternative embodiments of the present invention can be fabricated using a translation apparatus that moves a stimulus producing light beam over a surface (for example, a plane) that is substantially parallel to a back surface of projection screen 105. FIG. 1B shows a block diagram of stimulus projection system 131 that is mounted on a mechanical arm (not shown), which stimulus projection system 131 can be moved (in response to input signals from a controller) in a plane parallel to projection screen 105 in either X-Y coordinates (indicated by arrows 156), or in polar coordinates. Many methods and apparatus are well known to those of ordinary skill in the art for use in fabricating a controller-controlled mechanism that can provide such motion in a plane. For example, it is well known how to provide an X-Y type motion in a plane like a plotter device utilizing, for example, a pair of motors (one motor for providing motion along an X-axis, and one motor for providing motion along a Y-axis). In addition, it is well known in the art how to provide a polar coordinate type motion in a plane utilizing, for example, two motors, a rotation arm apparatus, and a carrier that travels on the rotation arm apparatus (one motor for providing rotation of the rotation arm apparatus, and one motor for providing motion of the carrier along the rotation arm apparatus). Stimulus projection system 131 comprises a light source, for example, like light source 101 described above in conjunction with FIG. 1A, and a projection lens system.

Advantageously, in accordance with such an embodiment, the distance between stimulus projection system 131 and projection screen 105 will be substantially the same distance as stimulus projection system 131 is moved. As a result, the depth of focus of the projection lens system comprising stimulus projection system 131 can have a depth of focus that is smaller than that of projection lens system 102 of FIG. 1A. Thus, the numerical aperture of the projection lens system can be increased to increase the brightness of the stimulus produced by stimulus projection system 131.

In accordance with a further aspect of the embodiment shown in FIG. 1B, stimulus projection system 131 is mounted on a further mechanical arm (not shown) to provide a tilting mechanism. In accordance with this further aspect, the further mechanical arm can move (in response to input signals from a controller) in a direction causes light output from stimulus projection system 131 to be directed toward the center of magnifier lens 107 (see FIG. 1A) of the stimulus viewing system. Such a tilting mechanism can be used when stimulus projection system 131 is mounted to move in X-Y coordinates or when it is mounted on a rotation arm to move in polar coordinates. In accordance with this further aspect, varying the tilt angle can advantageously compensate for brightness differences that might occur when stimulus projection system 131 is moved to various locations over a surface that is substantially parallel to a back surface of projection screen 105. For example, without varying the tilt angle, the brightness of the stimulus, as perceived by the test eye, may be different when the position of the stimulus changes from a central position on projection screen 105 to a peripheral position on projection screen 105. In fabricating an embodiment in accordance with this further aspect, the depth of focus of the projection lens system should be designed to be large enough to account for differences in distance between stimulus projection system 131 and projection screen 105 caused by differences in tilt angle at different positions of stimulus projection system 131 (advantageously, this will ensure that the stimulus is in focus when stimulus projection system 131 is moved to the different positions).

Figure 1C:
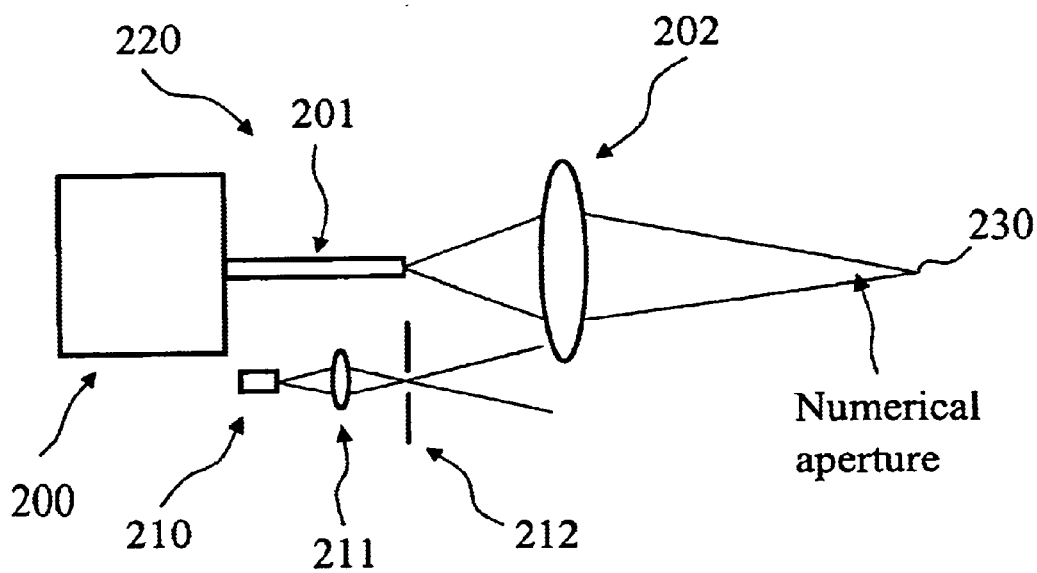
FIG. 1C shows a block diagram of alternative embodiments of a stimulus projection system that can be utilized to fabricate a back projection visual field tester in accordance with one or more embodiments of the present invention.

FIG. 1C shows a block diagram of stimulus projection system 220 that is fabricated in accordance with an alternative embodiment of the present invention. Stimulus projection system 220 may replace a portion of the stimulus projection system comprised of light source 101 and stimulus projection lens system 102 shown in FIG. 1A, or it may serve as stimulus projection system 131 shown in FIG. 1B. As shown in FIG. 1C, bright, white light source 200 (such as, for example, an arc lamp, a Halogen lamp, or any one of a number of other light sources that are well known to those of ordinary skill in the art) outputs light that is coupled into optical fiber 201, and light output from optical fiber 201 is transmitted, in turn, by stimulus projection lens system 202 to location 230 to form a stimulus. Although stimulus projection lens system 202 is shown as being comprised of one lens, those of ordinary skill in the art will readily understand that stimulation projection lens system 202 may comprise one or more lenses. In an alternative embodiment, stimulus projection system 220 may comprise white LED 210 (or other small emitting area light sources that are well known to those of ordinary skill in the art), condensing lens system 211, and aperture 212 to form a stimulus in place of bright, white light source 200 and optical fiber 201. For this alternative embodiment, light emanating from aperture 212 is transmitted by stimulus projection lens system 202 to location 230 to form a stimulus.

For embodiments of the present invention shown in FIG. 1C that are utilized, for example, with a turning mirror (like gimbal-mounted, turning mirror 103 shown in FIG. 1A) to move the stimulus over projection screen 105, stimulus projection lens system 202 is preferably designed to have such a long depth of focus that the image of a light aperture (for example, the image of optical fiber 201 or the image of aperture 212), and, thereby, the stimulus, is well focused over the entire area of projection screen 105. To do this, in accordance with one embodiment of the present invention, one designs stimulus projection lens system 202 (in accordance with any one of a number of methods that are well known to those of ordinary skill in the art) to have a numerical aperture (i.e., as shown in FIG. 1C, the angle subtended from location 230 to stimulus projection lens system 202) that is small enough to achieve the desired long depth of focus. However, embodiments of the present invention shown in FIG. 1C that are utilized with embodiments of the present invention that are fabricated in accordance with a teaching described above in conjunction with FIG. 1B, may be advantageously used without a stimulus projection lens system having a long depth of focus.

Referring back to FIG. 1A, light source 106 substantially uniformly illuminates projection screen 105 with light. Light source 106 may comprise LEDs, tungsten lamps, Halogen lamps, a fluorescent lamp, and so forth. For example, in some embodiments, light source 106 may comprise a number of light sources, and in other embodiments it may comprise a light source in the form of, for example, a ring. In addition, in accordance with one embodiment, an interface apparatus (not shown) is disposed between controller 150 and light source 106 in a manner which is well known to those of ordinary skill in the art. Then, in accordance with methods that are well known to those of ordinary skill in the art, for example, under software control, controller 150 sends signals through the interface apparatus to light source 106 to cause it to emit light. In accordance with methods that are well known to those of ordinary skill in the art, controller 150, under software control, controls output from light source 106 as to one or more of: (a) duration of an illumination interval; (b) intensity of illumination during the illumination interval; and (c) color. For example, color may be controlled by use of filters in a manner that is well known to those of ordinary skill in the art. Further, the control input for controller 150 can result from predetermined criteria and/or from user input by means of a user interface (not shown) in accordance with any one of a number of methods that are well known to those of ordinary skill in the art.

In accordance with further embodiments of the present invention, blue filters can be placed in the optical path of the stimulus projection system to generate a blue stimulus; and background illumination light source 106 can be either a yellow LED or a white light source covered with a yellow filter to generate a desired yellow background for a short-wavelength, standard automatic perimeter (SWAP) test.

Figure 2:
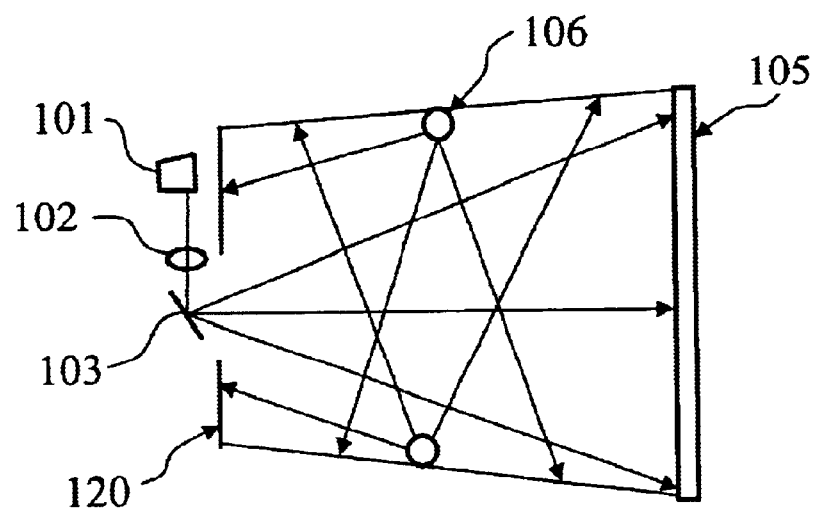
FIG. 2 shows a block diagram of an alternative embodiment of a background illumination system that can be utilized to fabricate a back projection visual field tester in accordance with one or more embodiments of the present invention.

FIG. 2 shows a block diagram of an alternative embodiment of a background illumination system that can be utilized to fabricate a back projection visual field tester in accordance with one or more embodiments of the present invention. As shown in FIG. 2, light source 106 directs light at walls 120 of an enclosure of a back of projection screen 105. In one such embodiment, walls 120 of the enclosure have a white, rough surface which serves, as shown in FIG. 2, as an integrating sphere to provide uniform background illumination for projection screen 105. Many other method and apparatus are well known to those of ordinary skill in the art for providing such a result. In using such embodiments, projection screen 105 is: (a) substantially uniformly illuminated by light from light source 106 and walls 120; and (b) illuminated by stimuli 104 generated by the stimulus projection system comprised of light source 101, stimulus projection lens system 102, and turning mirror 103 where one or more of: (i) duration of an illumination interval; (ii) intensity of illumination during the illumination interval; and (iii) color are determined by, for example, controller 150 in accordance with predetermined criteria and/or in response to user input. In addition, one or more of: (a) duration of an illumination interval; (b) intensity of illumination during the illumination interval; and (c) color of light source 106 are determined by, for example, controller 150 in accordance with predetermined criteria and/or in response to user input.

Referring back to FIG. 1A, projection screen 105 is viewed through a stimulus viewing system by a patient whose test eye is located at position 108. Position 108 is substantially at a center of a viewing box (not shown) which is, for example, a cone shaped enclosure. As shown in FIG. 1A, the stimulus viewing system for back projection visual field tester 100 comprises magnifier lens system 107 (those of ordinary skill in the art will readily understand that magnifier lens system 107 may comprise one or more lenses).

In accordance with one embodiment of the present invention, the focal length of magnifier lens system 107 and physical distance 111 (i.e., the distance between projection screen 105 and magnifier lens system 107) are selected so that projection screen 105 is imaged at a distance about 30 cm away from the patient's test eye to reduce strain. In accordance with such an embodiment, an embodiment of back projection visual field tester 100 can be fabricated where the physical distance 111 between projection screen 105 and magnifier lens system 107 is much shorter than the 30 cm distance required for a patient to see comfortably. Advantageously, this enables the size of projection screen 105 and back projection visual field tester 100 to be substantially reduced over visual field testers fabricated in accordance with the prior art. To understand the magnitude of such a reduction, assume that distance 111 between projection screen 105 and magnifier lens system 107 is chosen to be 15 cm. In such a case, the total volume of the viewing optical space would be only ⅛ of the volume if projection screen 105 were physically located 30 cm away from the patient's eye.

A visual field tester fabricated in accordance with one embodiment of the present invention may further comprise an apparatus for providing a fixation target or for fixing the position of a patient's test eye (such apparatus is not shown in FIG. 1A so that the operation of the remainder of the disclosed back projection visual field tester can more easily be understood). Such a fixation apparatus would engage the attention of the test eye, and may be fabricated in accordance with any one of a number of methods that are well known to those of ordinary skill in the art. For example, a fixation device may be an LED which is disposed at a predetermined location for viewing by the patient's test eye. Alternatively, a black dot or a predetermined pattern, for example and without limitation, a diamond shaped pattern, can be painted on a center of projection screen 105 to serve as a fixation target during a central vision test. Further, a pair of predetermined fixation patterns can be painted on both horizontal and vertical edges of projection screen 105 to serve as fixation targets during a peripheral vision test.

Lastly, as is well known to those of ordinary skill in the art, in order to fabricate a visual field tester in accordance with the present invention, the patient is provided with an apparatus, for example, indication apparatus 118 in FIG. 1A, for use in indicating a patient's perception of the presence or absence of optical radiation impinging upon the eye. As is well known, such indication apparatus may include a button which, when depressed, sends a signal to controller 150. Such an indication apparatus may also include foot pedals, mouses, and the like. Lastly, controller 150 may be configured in accordance with any one of a number of methods that are well known to those of ordinary skill in the art to cause the stimuli and the background illumination to be generated in patterns, for example, predetermined patterns, suitable to any number of visual tests and to collect the patient's input to produce, as output, measurements, for example, of the patient's visual sensitivity.

Figure 3A:
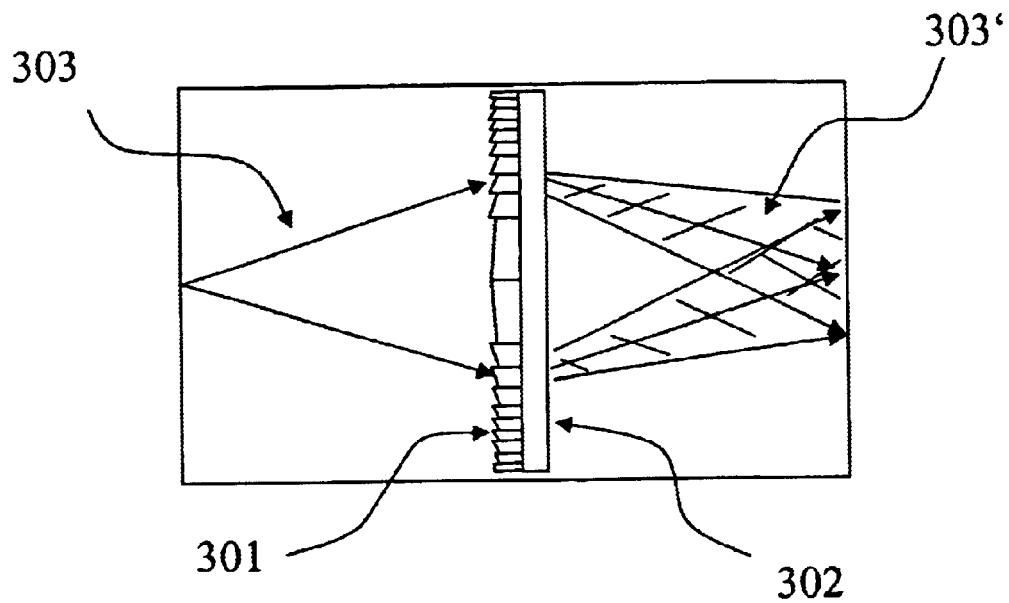
FIG. 3A shows a diagram of one embodiment of a projection screen that can be utilized to fabricate a back projection visual field tester in accordance with one or more embodiments of the present invention.

FIG. 3A shows a diagram of one embodiment of projection screen 105 (shown in FIG. 1A) that can be utilized to fabricate a back projection visual field tester in accordance with one or more embodiments of the present invention. In accordance with one such embodiment of the present invention, projection screen 300 provides two functions. In accordance with a first function, projection screen 300 (by action of lens 301) acts as a lens or a prism. As such, projection screen 300 (by action of lens 301) directs optical beam 303 (representing light from the stimulus and from the background illumination) towards location 108 (as shown in FIG. 1A) where the patient's test eye is placed. In accordance with a second function, projection screen 300 (by action of diffuse light shaper 302) diffuses or expands optical beam 303' that is output from projection screen 300 into a predetermined divergence angle. Because projection screen 300 is transparent, and in a preferred embodiment it is highly transparent (for example, it may be readily fabricated from a plastic material such as polycarbonate, Polyseter, and the like), not much light is lost to absorption by the material comprising projection screen 105. In accordance with this embodiment of the present invention, the divergence angle of optical beam 303' is controlled so that optical beam 303' will substantially cover an aperture of magnifier lens system 107 (see FIG. 1A). As a result, not much light will be vignetted by the aperture of magnifier lens system 107. Hence, since most of the light is directed into magnifier lens system 107 and, in turn, the patient's test eye, a high efficiency projection system is achieved. In accordance with one embodiment of the present invention, projection screen 105 can be fabricated by physically laminating two optical components together, namely, Fresnel lens 301, and light diffuser 302, each of which components substantially performs the first and second functions described above, respectively.

Figure 3B:
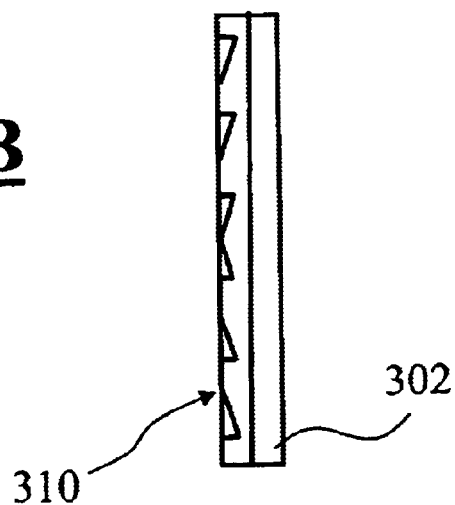
FIG. 3B shows a diagram of an alternative embodiment of a projection screen that can be utilized to fabricate a back projection visual field tester in accordance with one or more embodiments of the present invention.

FIG. 3B shows a diagram of another embodiment of projection screen 105 that can be utilized to fabricate a back projection visual field tester in accordance with one or more embodiments of the present invention. In accordance with this embodiment of the present invention, projection screen 105 can be fabricated by laminating prism array 310 and light diffuser 302, each of which components substantially performs the first and second functions described above, respectively. However, because the prisms in prism array 310 are located at predetermined positions, this embodiment can be used for a fixed visual field test pattern wherein light impinges upon the areas of projection screen 105 at which the prisms are located.

As an alternative, projection screen 105 can be fabricated in one single piece wherein Fresnel lens 301 or prism array 310 are fabricated in one side of a screen material such as, for example, and without limitation, acrylic, polycarbonate, and the like. Then, light diffuser 302 is fabricated on the other side of the screen material in accordance with any one of a number of many methods that are well known to those of ordinary skill in the art. For example, light diffuser 302 can be a diffuser having a desired diffusing angle such as a roughened surface, or it can a "holographic diffuser/light shaper" that is manufactured by the Physical Optics Corporation of Torrance, Calif. Such alternative embodiments may be fabricated by forming a mold, and then by replicating the mold.

In an embodiment of projector screen 105 where projector screen 105 is highly transparent, an object located behind the screen (i.e., the object is located on a side of the screen opposite from the patient) will be seen by the patient if the object is close to the screen. In fact, the object will be more easily seen if it has high contrast, i.e., it is black or another color. As those of ordinary skill in the art will appreciate, this is not desirable for a visual field tester. One way of avoiding this is to design the stimulus projection system, for example, the stimulus projection systems shown in FIGS. 1A, 1B, and 1C, to have a long working distance so that the stimulus projection system is far enough from projection screen 105 not to be seen readily. Additionally, the body of the stimulus projection system can also be painted the same color as the wall of an enclosure, thereby reducing its contrast when compared with the background illumination.

Figure 4:
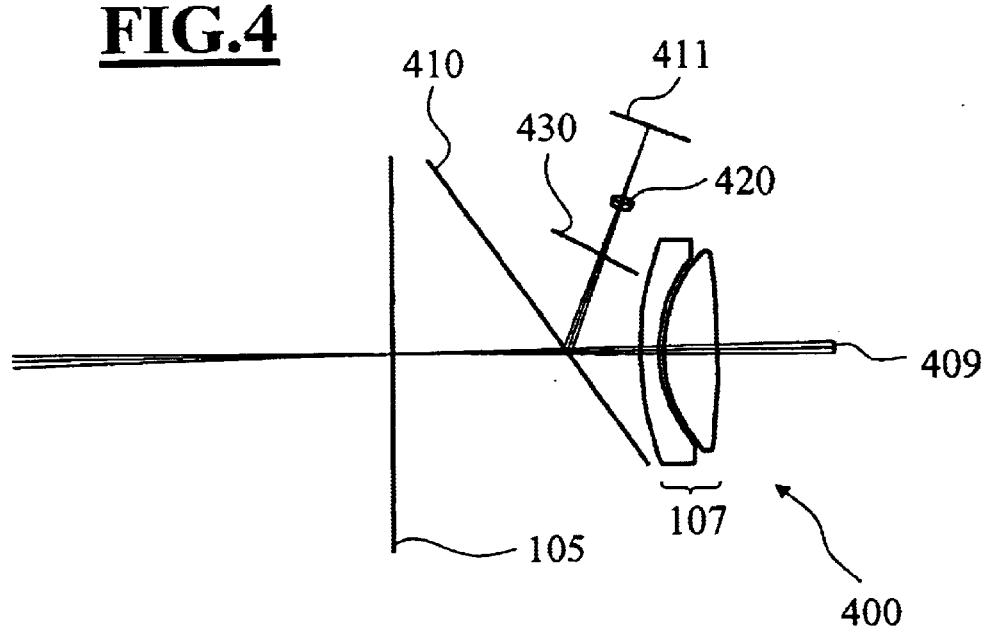
FIG. 4 shows a block diagram of an alternative embodiment of a stimulus viewing system that can be utilized to fabricate one or more embodiments of the present invention.

FIG. 4 shows a block diagram of an alternative embodiment of a stimulus viewing system that can be utilized to fabricate one or more embodiments of the present invention. For the most part, stimulus viewing system 400 is the same as the stimulus viewing system shown in FIG. 1A in that it comprises magnifier lens system 107. However, a source of test radiation (for example, a source of infrared radiation that is fabricated in accordance with any one of a number of methods that are well known to those of ordinary skill in the art and is not shown) is directed at a patient's test eye plane 409 (for example, in one embodiment the source of test radiation may be located so that test radiation output from the source is directed to the patient's test eye plane 409 by reflection from beamsplitter 410). In accordance with one embodiment, beamsplitter 410 is fabricated in accordance with any one of a number of methods that are well known to those of ordinary skill in the art to transmit light such as light from the stimulus and the background illumination, and to reflect the test radiation. Test radiation reflected from the patient's test eye passes through magnifier lens system 407, is reflected by beamsplitter 410, passes through filter 430, and is imaged to CCD camera 411 by lens system 408 (those of ordinary skill in the art will readily understand that lens system 408 may comprise one or more lenses). Filter 430 may be fabricated in accordance with any one of a number of methods that are well known to those of ordinary skill in the art to transmit radiation in a band of wavelengths substantially encompassing wavelengths of the test radiation. For example, filter 430 may be fabricated to transmit infrared radiation. Filter 430 may be placed in positions other than that shown in FIG. 4 and still serve to inhibit passage of radiation other than the test radiation to CCD camera 411. An image output from CCD camera 411 may be displayed on a video monitor (not shown in FIG. 4) for monitoring purposes. In addition, as has been disclosed in the prior art, CCD camera 411 can also be used as an eye tracking device either by analyzing a location of the image of the eye in accordance with any one of a number of methods that are well known to those of ordinary skill in the art, or by analyzing a reflection of a point light source illumination (not shown) in accordance with any one of a number of methods that are well known to those of ordinary skill in the art. Those of ordinary skill in the art will readily appreciate that CCD camera 411, as shown in FIG. 4, can be used with any of the embodiments described herein.

Figure 5:
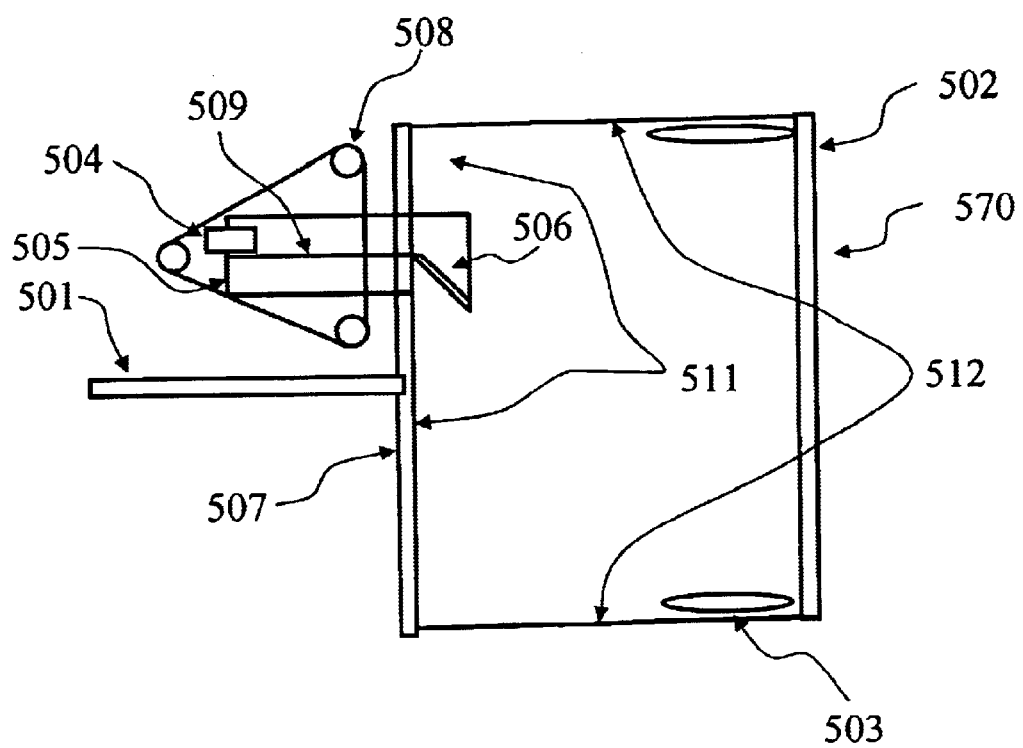
FIG. 5 shows a block diagram of an alternative embodiment of a stimulus projection system and a background illumination system that can be utilized to fabricate a back projection visual field tester in accordance with one or more embodiments of the present invention.
Figure 6:
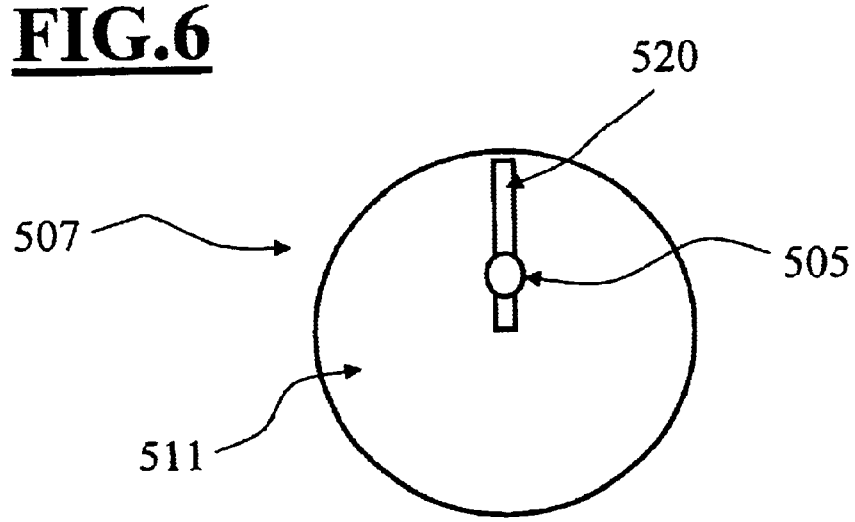
FIG. 6 shows a diagram of a front view of a portion of the stimulus projection system and background illumination system shown in FIG. 5.

FIG. 5 shows a block diagram of an alternative embodiment of a stimulus projection system and a background illumination system that can be utilized to fabricate a back projection visual field tester in accordance with one or more embodiments of the present invention. FIG. 6 shows a front view of a portion of the system. As shown in FIG. 6, projection optics assembly 505 is mounted on disk 507, and projection optics assembly 505 is moved by a motor (not shown) in response to input signals from a controller in a radial direction in slot 520 disposed in disk 507. As shown in FIG. 5, disk 507 is rotated by a motor (not shown) that is connected to shaft 501 in response to input signals from the controller. In this manner, a stimulus is produced by light output from projection optics assembly 505 that impinges upon projection screen 502, and the stimulus is moved in polar coordinates (i.e., r, θ).

As shown in FIG. 5, an interior surface is formed by front surface 511 of disk 507, interior surfaces 512 of an enclosure, and a back surface of projection screen 502. The interior surface is made into a light integrating surface by fabricating front surface 511 of disk 507, and interior surfaces 512 of the enclosure to have substantially the same color. For example, front surface 511 of disk 507 and interior surfaces 512 of the enclosure may all be the same white color. As further shown in FIG. 5, one or more light sources 503 such as, for example, one or more fluorescent lamps, one or more LEDs, one or more Tungsten lamps, one or more Halogen lamps, and so forth are used to illuminate the light integrating surface. As was the case for embodiments described above, output from projection optics assembly 505 and light source 503 is controlled by a controller in a manner like that described above.

In accordance with a further aspect of such alternative embodiments, as shown in FIG. 5, projection optics assembly 505 protrudes through an aperture in a strip of material 508 (having substantially the same color as front surface 511 of disk 507). The strip of material 508 is wider than slot 520, and is disposed to cover slot 520. Further, strip of material 508 rotates on rollers behind slot 520 (the rotation being produced, for example, by the same motor that causes movement of projection optics assembly 505) whenever projection optics assembly 505 slides along slot 520. As a result, except for a lens aperture of projection optics assembly 505, all other surfaces in the enclosure are fabricated to have substantially the same color as strip 508 and front surface 511 of disk 507, for example, white, or any other desired background illumination color for a visual field test.

In accordance with a still further aspect of such alternative embodiments, beamsplitter 506 is placed in front of projection optics assembly 505 to cover the lens aperture of projection optics assembly 505. LED 504 outputs light into light integrating cylinder 509 whose interior surfaces have the same color as the desired background illumination. Light integrating cylinder 509 homogenizes light output from LED 504, and the homogenized light is reflected by beamsplitter 506 to mask the lens aperture of projection optics assembly 505, i.e., the homogenized light illuminates an area that covers the lens aperture, which area would otherwise be seen by the patient through projection screen 502. In addition, in accordance with one embodiment, an interface apparatus (not shown) is disposed between a controller and LED 504 in a manner which is well known to those of ordinary skill in the art. Then, in accordance with methods that are well known to those of ordinary skill in the art, for example, under software control, the controller sends signals through the interface apparatus to LED 504 to cause it to emit light. In accordance with methods that are well known to those of ordinary skill in the art, the controller, under software control, controls output from LED 504 as to one or more of: (a) duration of an illumination interval; (b) intensity of illumination during the illumination interval; and (c) color. For example, color may be controlled by use of filters in a manner that is well known to those of ordinary skill in the art. Further, the control input for the controller can result from predetermined criteria and/or from user input by means of a user interface (not shown) in accordance with any one of a number of methods that are well known to those of ordinary skill in the art. By controlling the color of light integrating cylinder 509, the brightness of light output from light integrating cylinder 509, the reflectivity of beamsplitter 506 for light output from LED 504, and the transmissivity of beamsplitter 506 for light output from projection optics assembly 505, the lens aperture of projection optics assembly 505 may be blended into the background illumination. Still further, in accordance with one embodiment, the brightness of light output from light integrating cylinder 509 can be controlled by using the controller to control the output from LED 504.

Figure 7:
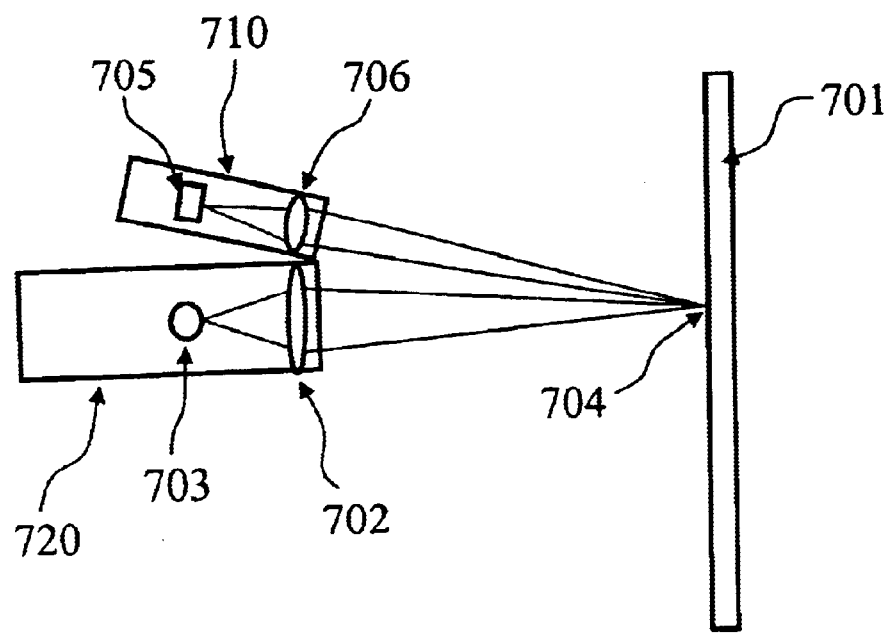
FIG. 7 shows a block diagram of an alternative embodiment of a light monitoring optical system that can be utilized to fabricate a back projection visual field tester in accordance with one or more embodiments of the present invention.

FIG. 7 shows a block diagram of an alternative embodiment of a light monitoring optical system that can be utilized to fabricate a back projection visual field tester in accordance with one or more embodiments of the present invention. As shown in FIG. 7, stimulus projection system 720 comprises aperture 703 of a light source (not shown) and projection lens system 702 (those of ordinary skill in the art will readily understand that projection lens system 702 may comprise one or more lenses). Note that aperture 703 is equivalent to aperture 212 shown in FIG. 1C, and the light source may comprise light source 210 and condenser lens system 211 also shown in FIG. 1C. As further shown in FIG. 7, projection lens system 702 projects light emitted from aperture 703 of the light source to stimulus location 704 on a back surface of projection screen 701. Those of ordinary skill in the art should appreciate that although one embodiment of stimulus projection system 720 is shown in FIG. 7 for purposes of illustrating this aspect of the present invention, further embodiments of the present invention exist where stimulus projection system 720 may be fabricated in accordance with any one of the embodiments described herein.

As further shown in FIG. 7, light monitoring optical system 710 comprises photodetector 705 and image lens system 706 (those of ordinary skill in the art will readily understand that image lens system 706 may comprise one or more lenses). In accordance with this embodiment, photodetector 705 is imaged to stimulus location 704 on the back surface of projection screen 701. Many methods are well known to those of ordinary skill in the art for coupling stimulus projection system 720 and light monitoring optical system 710 so they are imaged to the same location on the back surface of projection screen 701. For example, in accordance with one embodiment, they may be joined together by a mechanical arm.

Output from photodetector 705 may be applied as input to a controller, for example, controller 150 shown in FIG. 1A, and the controller can utilize the input to monitor, among other things, the brightness of the stimulus. In addition, by using the controller to control intervals when the stimulus is active, the brightness of the background illumination (as well as the brightness of the stimulus) at location 704 can be measured independently using output from photodetector 705. Then, in accordance with one embodiment of the present invention, using these measurements of brightness, contrast between the stimulus and the background illumination can be controlled accurately at specific locations on the back surface of projection screen 701 by changing one or both the stimulus brightness and the background brightness at the specific locations. An advantage of the embodiment shown in FIG. 7 is that use of separate optics paths for stimulus projection system 720 and light monitoring optical system 710 avoids issues relating to reflected light that occur when projection and monitoring optics share the same optical components.

Those skilled in the art will recognize that the foregoing description has been presented for the sake of illustration and description only. As such, it is not intended to be exhaustive or to limit the invention to the precise form disclosed.

What is claimed is:

1. A visual field tester comprises:
    a projection screen;
    a stimulus projection system that projects a light stimulus onto a first side of the projection screen;
    a background projection system that projects a background light onto the first side of the projection screen; and
    a lens system, disposed on a second side of the projection screen, that directs light transmitted through the projection screen to a predetermined location.

2. The visual field tester of claim 1 wherein the stimulus projection system comprises:
    a translation apparatus that is configured to move the stimulus projection system over a surface that is substantially parallel to a surface of the first side of the projection screen.

3. The visual field tester of claim 2 wherein the translation apparatus is configured to move the stimulus projection system in X-Y coordinates over a plane.

4. The visual field tester of claim 3 wherein the translation apparatus comprises two motors, one motor being configured to move the stimulus projection system along the X coordinate and another motor being configured to move the stimulus projection system along the Y axis.

5. The visual field tester of claim 2 wherein the translation apparatus is configured to move the stimulus projection system in polar coordinates over a plane.

6. The visual field tester of claim 5 wherein the translation apparatus comprises two motors, one motor being configured to move the stimulus projection system along a radial polar coordinate and another motor being configured to move the stimulus projection system along an angular polar coordinate.

7. The visual field tester of claim 2 which further comprises a tilting mechanism that is configured to direct light output from the stimulus projection system at varying angles with respect to the lens system depending on a position of the stimulus projection system on the surface.

8. The visual field tester of claim 1 wherein the background projection system comprises a source disposed in an enclosure that is configured to function substantially as a light integrating sphere.

9. The visual field tester of claim 8 wherein the enclosure comprises walls having a white, rough surface.

10. The visual field tester of claim 1 wherein the projection screen comprises:
   a prism array; and
   a diffuser element.

11. The visual field tester of claim 1 wherein the projection screen comprises:
   a Fresnel lens; and
   a light shaping diffuser element.

12. The visual field tester of claim 1 which further comprises:
   a beamsplitter disposed between the projection screen and the lens system;
   a source of test radiation whose output is directed toward the predetermined position;
   a lens group configured to relay reflected test radiation, which reflected test radiation light is reflected from a patient's eye disposed at the predetermined location; and
   a CCD camera disposed to collect the relayed test radiation.

13. The visual field tester of claim 12 that further comprises a monitor that displays an image output from the CCD camera.

14. The visual field tester of claim 12 wherein the source of test radiation is a source of infrared radiation and wherein the visual field tester further comprises a filter disposed to transmit the reflected test radiation and block radiation having wavelengths of the light transmitted through the projection screen.

15. The visual field tester of claim 1 wherein:
   the stimulus projection system comprises a disk having a slot and a stimulus source of light and a projection lens system configured to move in the slot; and
   the background projection system comprises an enclosure having walls and a source of the background light disposed therein, wherein a surface of the disk forms a portion of a surface of the enclosure.

16. The visual field tester of claim 15 wherein the surface of the disk, and surfaces of walls of the enclosure are substantially the same color.

17. The visual field tester of claim 16 wherein the stimulus projection system further comprises a strip of material that is wider than the slot and that moves as the source and projection lens move to provide a backing for the slot.

18. The visual field tester of claim 15 wherein the stimulus projection system further comprises a radiation source configured to output radiation that masks a lens aperture of the stimulus projection system.

19. The visual field tester of claim 18 wherein the radiation source comprises a masking source disposed in an integrating enclosure, and a beamsplitter disposed over the lens aperture that is configured to direct the radiation output from the integrating enclosure toward the projection screen, and to transmit light output from the stimulus source of light.

20. The visual field tester of claim 1 which further comprises:
   a photodetector disposed to detect light reflected from a location on the first side of the projection screen.

21. The visual field tester of claim 20 which further comprises a controller that controls the stimulus projection system, and the background projection system, and is responsive to output from the photodetector.

22. The visual field tester of claim 21 wherein the controller causes the photodetector to detect light reflected from the light stimulus at the location.

23. The visual field tester of claim 21 wherein the controller causes the photodetector to detect light reflected from the background light at the location.

24. The visual field tester of claim 1 wherein light source includes an LED, a Halogen lamp, a short arc Mercury lamp, a Xenon lamp, or a laser.

25. The visual field tester of claim 1 wherein the stimulus projection system comprises:
   a light source and an aperture that outputs light; and
   a projection lens system that projects light output from the aperture onto the projection screen;
   further comprising a controller wherein the aperture or its shape is changed in response to output from the controller.

26. The visual field tester of claim 25 wherein the controller controls output from light source 101 as to one or more of: (a) duration of an illumination interval; (b) intensity of illumination during the illumination interval; and (c) color.

27. The visual field tester of claim 26 wherein color is controlled by use of filters.

* * * * *